United States Patent [19]
Lewis et al.

[11] Patent Number: 5,668,153
[45] Date of Patent: Sep. 16, 1997

[54] PIPERIDINE DERIVATIVES AND THEIR USE AS THERAPEUTIC AGENTS

[75] Inventors: Richard Thomas Lewis, Harlow; Angus Murray MacLeod, Bishops Stortford, both of England

[73] Assignee: Merck Sharp & Dohme, Ltd., Hoddesdon, England

[21] Appl. No.: 511,205

[22] Filed: Aug. 4, 1995

[30] Foreign Application Priority Data

Aug. 8, 1994 [GB] United Kingdom ............. 9415997

[51] Int. Cl.$^6$ .............. A61K 31/40; A61K 31/445; C07D 401/10; C07D 409/10
[52] U.S. Cl. .............. 514/323; 514/317; 514/319; 514/320; 514/324; 546/196; 546/201; 546/202; 546/205; 546/236
[58] Field of Search ............. 514/317, 319, 514/320, 323, 324; 546/196, 201, 202, 205, 236

[56] References Cited

U.S. PATENT DOCUMENTS

| | | | |
|---|---|---|---|
| 4,859,692 | 8/1989 | Berstein et al. | 514/381 |
| 5,270,324 | 12/1993 | Zamboni et al. | 514/311 |

FOREIGN PATENT DOCUMENTS

WO 93/14084  1/1993  WIPO.

OTHER PUBLICATIONS

Maggi et al. "Tachykinin receptors and tachykinin receptor antagonists" J. Auton. Pharmacol. v. 13, pp. 23–44 1993.

*Primary Examiner*—Ceila Chang
*Attorney, Agent, or Firm*—Robert J. North; Melvin Winokur

[57] ABSTRACT

Compounds of formula (I)

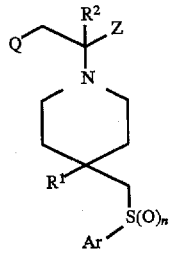

exemplified by formulae (Ia) and (Ib)

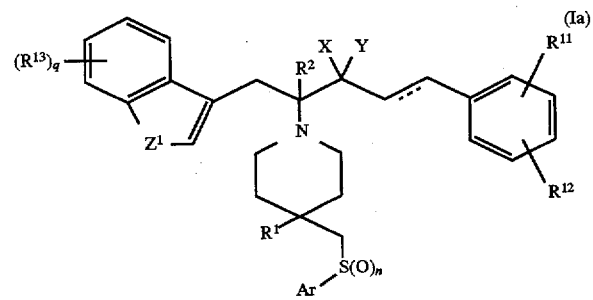

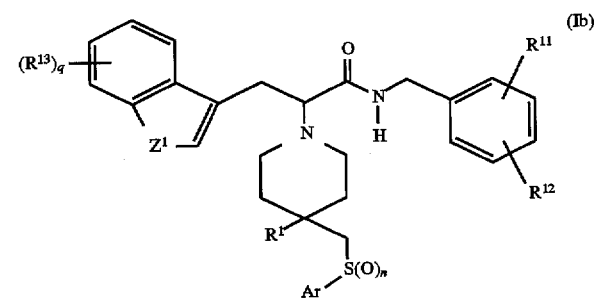

are tachykinin receptor antagonists useful in the treatment of disorders associated with the presence of an excess of tachykinins such as pain, inflammation, migraine, emesis and post herpetic neuralgia.

21 Claims, No Drawings

PIPERIDINE DERIVATIVES AND THEIR USE AS THERAPEUTIC AGENTS

This invention relates to a class of heterocyclic compounds, which are useful as tachykinin receptor antagonists.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

Phe-X-Gly-Leu-Met-$NH_2$

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (1987) 8, 506 . 510], specifically in the transmission of pain in migraine (B. E. B. Sandberg et al, *J. Med Chem*, (1982) 25, 1009) and in arthritis [Levine et al in *Science* (1984) 226, 547–549]. Tachykinins have also been implicated in gastrointestinal (GI) disorders and diseases of the GI tract such as inflammatory bowel disease [Mantyh et al in *Neuroscience* (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, 11 Nov. 1989 and Gronblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol.* *Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28th Jun.-2nd Jul. 1992], and in disorders of bladder function such as bladder detrusor hyper-reflexia (*Lancet*, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

International patent specification No. WO 93/14084, published 22nd Jul. 1993 discloses piperidine tachykinin antagonists of the general formula

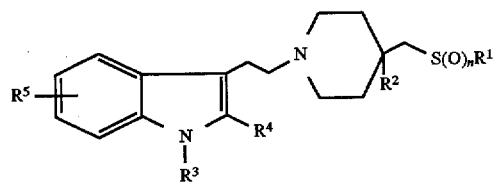

wherein $R^1$ is optionally substituted phenyl;

$R^2$ is hydrogen, hydroxy or $C_{1-4}$alkoxy;

$R^3$ is hydrogen or $C_{1-4}$alkyl;

$R^4$ is hydrogen, $C_{1-4}$alkyl or $C_{1-4}$alkoxy;

$R^5$ hydrogen, $C_{1-4}$alkyl, $CF_3$, CN or halogen; and n is zero, 1 or 2.

In essence, the present invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

The present invention provides a compound of formula (I), or a pharmaceutically acceptable salt or prodrug thereof:

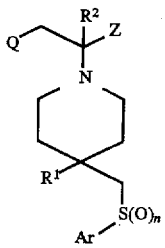
(I)

wherein

Q represents a phenyl group substituted by one or more halo, optionally substituted naphthyl, optionally substituted indolyl, optionally substituted benzthiophenyl, optionally substituted benzofuranyl, optionally substituted benzyl, or optionally substituted fluorenyl;

$R^1$ represents H, OH, $C_{1-6}$alkoxy or phenyloxy;

$R^2$ represents H, $C_{1-6}$alkyl or $C_{2-6}$alkenyl;

Z represents a group selected from

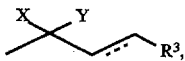
(a)

or

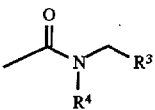
(b)

where one of X and Y represents H and the other represents hydroxy or $C_{1-6}$alkoxy, or X and Y together form a group =O or =NOR$^5$ where R$^5$ is H or $C_{1-6}$alkyl;

$R^3$ represents phenyl optionally substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl $C_{1-4}$alkyl, halo, cyano, nitro, trifluoromethyl, trimethylsilyl, OR$^a$, SR$^a$, SOR$^a$, NR$^a$R$^b$, NR$^a$COR$^b$, NR$^a$CO$_2$R$^b$, CO$_2$R$^a$ or CONR$^a$R$^b$, where R$^a$ and R$^b$ independently represent H, $C_{1-6}$alkyl, phenyl or trifluoromethyl;

$R^4$ represents H or $C_{1-6}$alkyl;

the dotted line represents an optional covalent bond;

Ar represents phenyl optionally substituted by 1 or 2 groups selected from $C_{1-6}$alkyl, $C_{1-6}$alkoxy, halo or trifluoromethyl; and n represents zero, 1 or 2.

As used herein, the definition of each expression, when it occurs more than once in any structure, is intended to be independent of its definition elsewhere in the same structure.

The alkyl, alkenyl and alkynyl groups referred to with respect to any of the above formulae may represent straight or branched groups. Thus, for example, suitable alkyl groups include methyl, ethyl, n- or iso- propyl, n-, sec-, iso- or tert-butyl.

The cycloalkyl groups referred to with respect to any of the above definitions include cyclopropyl, cyclobutyl, cyclopentyl or cyclohexyl. Similarly cycloalkyl-alkyl groups include cyclopropylmethyl.

Suitable alkenyl groups include vinyl and alkyl; and suitable alkynyl groups include propargyl.

For the avoidance of doubt, when covalent bond represented by the dotted line is present, the compounds of formula (I) contain an olefinic double bond.

The term "halo" as used herein includes fluoro, chloro, bromo and iodo, especially chloro and fluoro.

Where Q represents optionally substituted fluorenyl, the group is linked through the bridgehead carbon atom, that is to say, C-9 of the fluorenyl moiety.

Where Q represents optionally substituted naphthyl, indolyl, benzothiophenyl, benzofuranyl, benzyl or fluorenyl, suitable substituents include $C_{1-6}$alkyl, $C_{2-6}$alkenyl, $C_{2-6}$alkynyl, halo, cyano, nitro, trifluoromethyl, trimethylsilyl, SR$^a$, SOR$^a$, SO$_2$R$^a$, OR$^a$, NR$^a$R$^b$, NR$^a$COR$^b$, NR$^a$COOR$^b$, COOR$^a$ or CONR$^a$R$^b$, where R$^a$ and R$^b$ are as above defined. One or more substituents may be present and each may be located at any available ring position, except, where Q is optionally substituted indolyl, the nitrogen atom.

Where Q is optionally substituted indolyl, suitable nitrogen substituents include $C_{1-6}$alkyl, optionally substituted phenyl ($C_{1-4}$alkyl), COOR$^a$ or CONR$^a$R$^b$, wherein R$^a$ and R$^b$ are as above defined.

Suitable values of the group Q include 3,4-dichlorophenyl, 3-indolyl, 2-naphthyl, 3-naphthyl, 9-fluorenyl, benzyl, 3-benzothiophenyl and 3-benzofuranyl.

Preferably Q is 3-indolyl, 3-benzothiophenyl or 3,4-dichlorophenyl, more preferably 3-indolyl.

Suitably $R^1$ represents OH or methoxy, preferably methoxy.

Preferably $R^2$ represents H or methyl, more preferably H.

Where Z represents a group of formula (a), preferably the double bond is absent.

Suitably one of X and Y represents hydroxy or $C_{1-6}$alkoxy, such as methoxy, or X and Y together represent =O or =NOH. Preferably one of X and Y represents methoxy or X and Y together represent =O. More preferably, X and Y together represent =O.

Where Z represents a group of formula (b), preferably $R^4$ is H.

Where Z represents either a group of formula (a) or a group of formula (b), preferably $R^3$ represents substituted phenyl. Suitable phenyl substituents include nitro, trifluoromethyl, trimethylsilyl, bromo, chloro, fluoro, iodo, cyano, methyl, ethyl, cyclopropyl, vinyl, methoxy, phenoxy and amino. Preferably $R^3$ represents disubstituted phenyl.

Particularly preferred are compounds wherein $R^3$ represents 3,5-bis(trifluoromethyl)phenyl.

When Ar represents substituted phenyl, the substituent(s) may be present at any available ring position, thus the substituent(s) may be present at the 2-, 3-, 4-, 5- and/or 6-position of the phenyl ring.

When Ar represents phenyl substituted by two substituents, the substituents may be the same or different.

Suitable substituents on the phenyl ring represented by Ar include, in particular, $C_{1-4}$alkyl, especially methyl, $C_{1-4}$alkoxy, especially methoxy, trifluoromethyl and halo, especially fluorine or chlorine.

Preferably Ar is unsubstituted phenyl, 4-methylphenyl, or 2-methylphenyl, especially unsubstituted phenyl.

In the compounds of formula (I), n may represent zero (i.e. a sulphide), 1 (i.e. a sulphoxide) or 2 (i.e. a sulphone). n is preferably zero or 1, and especially 1. When n is 1, the (R)-sulphoxide is most preferred.

A particular sub-group of compounds according to the invention is represented by compounds of formula (Ia), and pharmaceutically acceptable salts and prodrugs thereof:

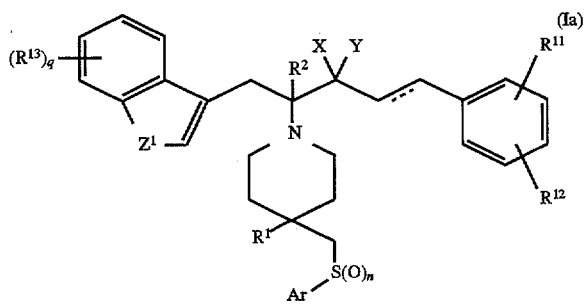

wherein $R^1$, $R^2$, X, Y, Ar and n are as defined for formula (I);

the dotted line represents an optional covalent bond;

$Z^1$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

$R^{11}$ and $R^{12}$ each independently represent H, $C_{1-6}$alkyl, $C_{2-6}$alkenyl, $C_{2-6}$alkynyl, $C_{3-7}$cycloalkyl, $C_{3-7}$cycloalkyl $C_{1-4}$alkyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined; and q is 0, 1, 2 or 3, preferably 0.

Another particular sub-group of compounds according to the invention is represented by compounds of formula (Ib), and pharmaceutically acceptable salts and prodrugs thereof:

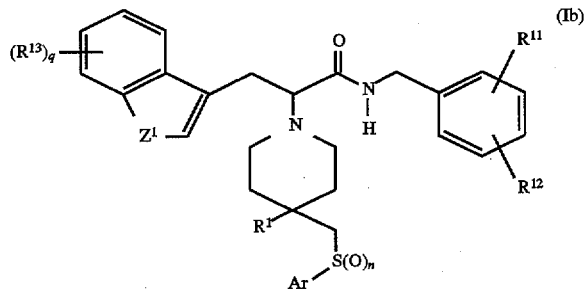

wherein $R^1$, Ar and n are as defined for formula (I);

$Z^1$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as previously defined), preferably S or NH;

$R^{11}$ and $R^{12}$ each independently represent H, $C_{1-6}$alkyl, $C_{2-6}$alkenyl, $C_{2-6}$alkynyl, $C_{3-7}$cycloalkyl, $C_{3-7}$cycloalkyl $C_{1-4}$alkyl, chloro, bromo, fluoro, iodo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as previously defined;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^a R^b$, where $R^a$ and $R^b$ are as previously defined; and q is 0, 1, 2 or 3, preferably 0.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when $R^1$ or $R^5$ is other than H, the nitrogen atom to which it is attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

The compounds according to the invention may exist both as enantiomers and as diastereomers. It is to be understood that all such isomers and mixtures thereof are encompassed within the scope of the present invention.

The invention also provides pharmaceutical compositions comprising one or more compounds of this invention in association with a pharmaceutically acceptable carrier.

Preferably these compositions are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic add, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric adds with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or off-in-water emulsion).

Suitable surface-active agents include, in particular, nonionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower off, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic and chemotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, postoperative, late phase or anticipatory emesis such as emesis induced by chemotherapy, radiation, toxins, viral or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders including motion sickness, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kuucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack. A preferred combination comprises the compounds of formula (I) with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta$2-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

Compounds of formula (I) may be prepared from intermediates of formula (II):

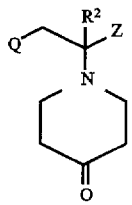

wherein Q, R², and Z are as defined for formula (I), by reaction with $CH_3S(O)_nAr$, where Ar and n are as defined for formula (I), after deprotonation with a strong base such as lithium hexamethyldisilylamide, lithium bis(trimethylsilyl) amide or lithium diisopropylamide.

The reaction is conveniently effected in a suitable solvent such as, an ether, for example, tetrahydrofuran, at a temperature between −78° C. and 30° C., for example, −70° C.

Intermediates of formula (II) may be prepared by reaction of a simple alkyl quaternary salt of 4-oxo-piperidine, especially 1,1-dimethyl-4-oxopiperidinium iodide, with a compound of formula (IIIA) or (IIIB):

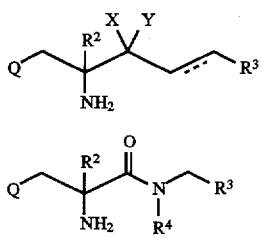

wherein Q, R², R³, R⁴, X, Y, Z and the dotted line are as defined for formula (I), in the presence of a base.

Suitable bases include alkali metal carbonates, such as, for example, potassium carbonate.

The reaction is conveniently effected in a suitable organic solvent, such as an alcohol, e.g. ethanol, suitably at elevated temperature.

Compounds of formula (IIIA), in which X and Y together represent =O and the double bond is present, may be prepared by the reaction of an aldehyde of formula $R^3CHO$ with a compound of formula (IV)

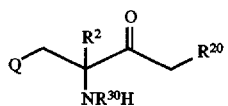

wherein Q and R² are as defined for formula (I), R²⁰ represents a group $PR^x_3$ or $PO(OR^x)_2$, wherein R* represents phenyl or $C_{1-10}$alkyl, and R³⁰ represents a suitable amine protecting group such as an aralkyloxycarbonyl group, especially benzyloxycarbonyl, or an alkoxycarbonyl group, especially tert-butoxycarbonyl (t-BOC), in the presence of a base.

Suitable bases include alkali metal hydrides, for example, sodium hydride, or alkali metal carbonates, for example, potassium carbonate.

The reaction is conveniently effected in a suitable organic solvent such as an ether, for example, tetrahydrofuran, or acetonitrile, suitably at ambient temperature.

Compounds of formula (IIIA), in which one of X and Y represents H and the other represents hydroxy, may be prepared from the corresponding compounds of formula (IIIA) wherein X and Y together represent =O, by reduction.

Suitable reducing agents include, for example, hydride reducing agents such as lithium aluminium hydride and sodium borohydride.

The reaction is conveniently carried out in a suitable organic solvent, such as an ether, e.g. tetrahydrofuran, suitably at ambient temperature.

Compounds of formula (IIIA) wherein one of X and Y represents H and the other represents $C_{1-6}$alkoxy may be prepared from the corresponding compounds of formula (IIIA) wherein one of X and Y represents H and the other represents hydroxy, by alkylation.

Suitable alkylation procedures include treatment of an alcohol of formula (IIIA) with an alkali metal hydride, such as sodium hydride, and a $C_{1-6}$alkylhalide. Suitable halides include, in particular, bromides and iodides.

The reaction is conveniently effected in an anhydrous organic solvent, for example, an ether, e.g. dimethoxyethane, suitably at ambient temperature.

Compounds of formula (IIIA) wherein X and Y together represent =$NOR^5$ may be prepared from the corresponding compounds of formula (IIIA) wherein X and Y together represent =O by the addition of hydroxylamine, or a derivative thereof. Compounds wherein R⁵ is other than H may be prepared from the corresponding compounds wherein R⁵ is H by alkylation, for example, using a diazo compound, such as diazomethane, or an alkyl halide or sulphate.

Compounds of formula (IIIA) wherein the double bond is absent may be prepared from the corresponding unsaturated compounds of formula (IIIA) by reduction.

Suitable reduction procedures include catalytic hydrogenation. Suitable hydrogenation catalysts include nobel metals, for example, platinum or palladium, or oxides thereof, which may be supported, for example, on charcoal. A preferred catalyst is Wilkinson's catalyst (tris (triphenylphosphine)rhodium(I)chloride).

The reaction is conveniently effected in a suitable organic solvent, such as an ether, e.g. tetrahydrofuran, an alcohol, e.g. ethanol, or an ester, e.g. ethyl acetate, suitably at ambient temperature.

Compounds of formula (IIIB) may be prepared by reaction of a compound of formula (V):

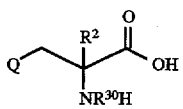

wherein Q and R² are as defined for formula (I) and R³⁰ is a protecting group as previously defined, with an amine of formula $HNR^4-CH_2R^3$, wherein R³ and R⁴ are as defined for formula (I).

The reaction is suitably effected in the presence of a base, such as a tertiary amine, for example, triethylamine, preferably in the presence of a suitable alkylchloroformate, such as t-butylchloroformate, conveniently in a suitable organic solvent, such as a halogenated hydrocarbon, e.g. dichloromethane. Alternatively, the reaction may be effected in the presence of a coupling agent, such as dicyclohexylcarbodiimide.

Compounds of formula (V) are commercially available or may be prepared using standard syntheses. Syntheses of amino acids are well documented and are described, for example, in *Chemistry and Biochemistry of the Amino Acids*, ed. G. C. Barrett, Chapman and Hall, 1985.

Compounds of formula (IV) may be prepared from compounds of formula (VI)

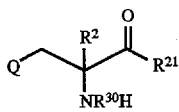
(VI)

wherein Q and $R^2$ are as defined for formula (I), $R^{30}$ is a protecting group as previously defined and $R^{21}$ represents an alkoxy or a suitably substituted amino group, such as a group $NR^yOR^z$, where $R^y$ and $R^z$ represent alkyl, in particular a group $NCH_3(OCH_3)$, by reaction with a compound of formula $CH_3PO(OR^x)_2$, where $R^x$ is an alkyl group, in the presence of a base.

Suitable reaction procedures will be readily apparent to the skilled person.

Suitable bases of use in the reaction include alkyl lithiums, such as butyl lithium.

Compounds of formula (VI) are commercially available or may be prepared using standard procedures well known to the skilled person in the art. The compounds of formula (VI) are amino acid derivatives. Syntheses of amino acids and derivatives thereof are well documented and are described, for example, in *Chemistry and Biochemistry of the Amino Acids*, ed. G. C. Barrett, Chapman and Hall, 1985.

A particularly convenient synthesis of compounds of formula (I) wherein Z represents a group of formula (a), involving the necessary steps of protection and deprotection, is illustrated by the following scheme:

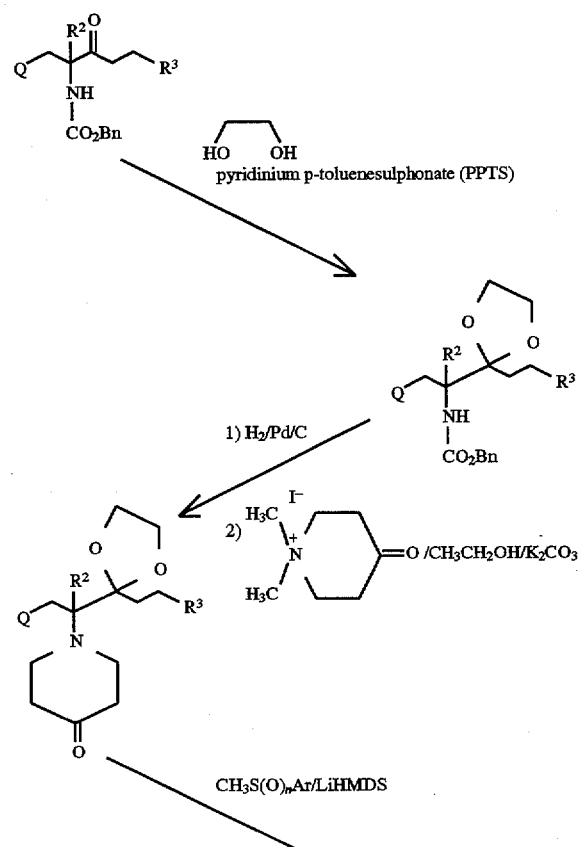

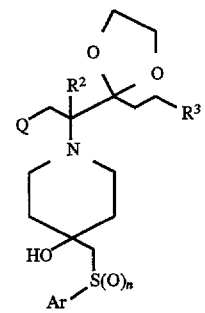

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The compounds of this invention may be formulated as specifically illustrated at pages 28 to 29 of European Patent Specification No. EP-A-0 528 495.

We claim:

1. A compound of the formula (I), or a pharmaceutically acceptable salt or prodrug thereof:

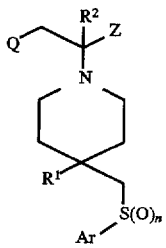

(I)

wherein

Q represents a phenyl group substituted by one or more halo, optionally substituted naphthyl, optionally substituted indolyl, optionally substituted benzthiophenyl, optionally substituted benzofuranyl, optionally substituted benzyl, or optionally substituted fluorenyl; wherein the optional substituents are selected from $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $CO_2R^a$ or $CONR^aR^b$, where $R^a$ and $R^b$ are as defined below; and where Q is optionally substituted indolyl, the nitrogen substituent is selected from $C_{1-6}$alkyl, optionally substituted phenyl($C_{1-4}$alkyl), $CO_2R^a$ or $CONR^aR^b$, where $R^a$ and $R^b$ are as defined below;

$R^1$ represents H, OH, $C_{1-6}$alkoxy or phenyloxy;

$R^2$ represents H, $C_{1-6}$alkyl or $C_{2-6}$alkenyl;

Z represents a group selected from

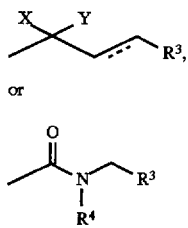

(a)

or (b)

where one of X and Y represents H and the other represents hydroxy or $C_{1-6}$alkoxy, or X and Y together form a group $=O$ or $=NOR^5$ where $R^5$ is H or $C_{1-6}$alkyl;

$R^3$ represents phenyl optionally substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ independently represent H, $C_{1-6}$alkyl, phenyl or trifluoromethyl;

$R^4$ represents H or $C_{1-6}$alkyl;

the dotted line represents an optional covalent bond;

Ar represents phenyl optionally substituted by 1 or 2 groups selected from $C_{1-6}$alkyl, $C_{1-6}$alkoxy, halo or tirfluoromethyl, and n represents zero, 1 or 2.

2. A compound as claimed in claim 1 of formula (Ia), or a pharmaceutically acceptable salt or prodrug thereof:

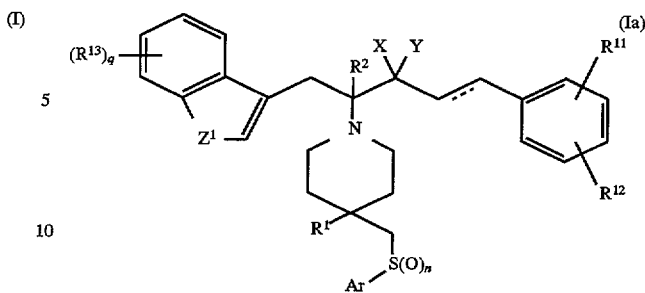

(Ia)

wherein $R^1$, $R^2$, X, Y, Ar and n are as defined in claim 1;

the dotted line represents an optional covalent bond;

$Z^1$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as defined in claim 1);

$R^{11}$ and $R^{12}$ each independently represent H, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as defined in claim 1;

each $R^{13}$ may occupy any available carbon atom of the bicyclic ring system and independently represents $C_{1-6}$alkyl, $C_{2-8}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as defined in claim 1; and q is 0, 1, 2 or 3.

3. A compound as claimed in claim 1 of the formula (Ib), or a pharmaceutically acceptable salt or prodrug thereof:

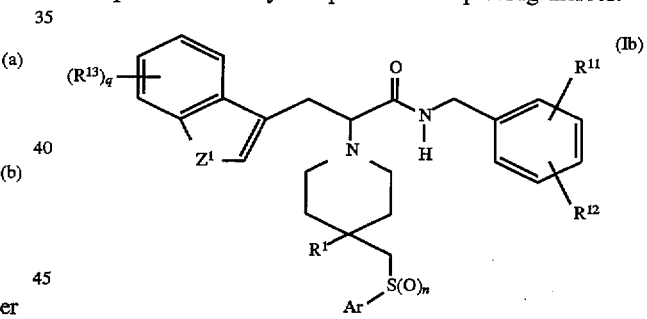

(Ib)

wherein $R^1$, Ar and n are as defined in claim 1;

$Z^1$ represents O, S or $NR^{14}$ (where $R^{14}$ is H, $C_{1-6}$alkyl, optionally substituted phenyl($C_{1-4}$alkyl), $CO_2R^a$ or $CONR^aR^b$, where $R^a$ and $R^b$ are as defined in claim 1);

$R^{11}$ and $R^{12}$ each independently represent H, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, chloro, bromo, fluoro, iodo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as defined in claim 1;

each $R^{13}$ may occupy any available carbon atom of the bicyclic ring system and independently represents $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $NR^aR^b$, $NR^aCOR^b$, $NR^aCO_2R^b$, $CO_2R^a$ or $CONR^aR^b$, where $R^a$ and $R^b$ are as defined in claim 1; and q is 0, 1, 2 or 3.

4. A compound as claimed in claim 1 wherein Q is 3-indolyl, 3-benzothiophenyl or 3,4-dichlorophenyl.

5. A compound as claimed in claim 2 or claim 3 wherein $Z^1$ represents S or NH.

6. A compound as claimed in claim 1 wherein $R^1$ represents OH or methoxy.

7. A compound as claimed in claim 1 wherein $R^2$ represents H or methyl.

8. A compound as claimed in claim 1 wherein the double bond is absent.

9. A compound as claimed in claim 1 wherein one of X and Y represents methoxy or X and Y together represent =O.

10. A compound as claimed in claim 1 wherein $R^4$ represents a hydrogen atom.

11. A compound as claimed in claim 1 wherein $R^3$ represents disubstituted phenyl.

12. A compound as claimed in claim 11 wherein $R^3$ represents 3,5-bis(trifluoromethyl)phenyl.

13. A compound as claimed in claim 1 wherein Ar represents unsubstituted phenyl, 4-methylphenyl, or 2-methylphenyl.

14. A compound as claimed in claim 1 wherein n is zero or 1.

15. A pharmaceutical composition comprising a compound as claimed in claim 1 or a pharmaceutically acceptable salt or prodrug thereof in association with a pharmaceutically acceptable carrier or excipient.

16. A method for the treatment or prevention of pain, inflammation, migraine, emesis or postherpetic neuralgia, which method comprises administration to a patient in need thereof of a tachykinin reducing amount of a compound according to claim 1, or a pharmaceutically acceptable salt or prodrug thereof.

17. A method according to claim 16 for the treatment or prevention of pain or inflammation.

18. A method according to claim 16 for the treatment or prevention of migraine.

19. A method according to claim 16 for the treatment or prevention of emesis.

20. A method according to claim 16 for the treatment or prevention of postherpetic neuralgia.

21. A process for the preparation of a compound of formula (I) as claimed in claim 1, which comprises:

(A) reacting a compound of formula (II):

(II)

wherein Q, $R^2$, and Z are as defined in claim 1, with $CH_3S(O)_n Ar$, where Ar and n are as defined in claim 1;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt or prodrug thereof.

* * * * *